United States Patent
Butler et al.

(10) Patent No.: US 9,301,905 B2
(45) Date of Patent: Apr. 5, 2016

(54) SALIVA-CURED DENTAL RESTORATIVE MATERIAL

(75) Inventors: David V. Butler, West Covina, CA (US); Karla S. Somerville, Upland, CA (US); Jan A. Orlowski, Altadena, CA (US)

(73) Assignee: Scientific Pharmaceuticals, Inc., Pomona, CA (US)

( * ) Notice: Subject to any disclaimer, the term of this patent is extended or adjusted under 35 U.S.C. 154(b) by 439 days.

(21) Appl. No.: 12/854,764

(22) Filed: Aug. 11, 2010

(65) Prior Publication Data

US 2012/0040310 A1    Feb. 16, 2012

(51) Int. Cl.
*A61C 5/04*   (2006.01)
*A61K 6/06*   (2006.01)
*A61K 6/083*  (2006.01)

(52) U.S. Cl.
CPC ............ *A61K 6/0625* (2013.01); *A61K 6/0612* (2013.01); *A61K 6/0631* (2013.01); *A61K 6/0835* (2013.01)

(58) Field of Classification Search
CPC . A61K 6/0612; A61K 6/0625; A61K 6/0631; A61K 6/0835
USPC .................................. 523/109, 116; 106/35
See application file for complete search history.

(56) References Cited

U.S. PATENT DOCUMENTS

| | | |
|---|---|---|
| 3,837,865 A | 9/1974 | Pellico |
| 4,518,430 A | 5/1985 | Brown et al. |
| 4,612,053 A | 9/1986 | Brown et al. |
| 5,051,130 A | 9/1991 | Futami et al. |
| 6,284,030 B1* | 9/2001 | Orlowski et al. ............... 106/35 |
| 2005/0171233 A1* | 8/2005 | Bublewitz et al. ............ 523/116 |
| 2005/0250871 A1* | 11/2005 | Bublewitz et al. ............ 523/109 |

* cited by examiner

*Primary Examiner* — Shuangyi Abu Ali
(74) *Attorney, Agent, or Firm* — Knobbe Martens Olson & Bear LLP

(57) ABSTRACT

Disclosed herein are dental temporary filling material and cement formulations comprising a hydrophobic matrix of a hydrophobic material in which an inorganic hardening material and fine, hydrophilic, water-insoluble solid particles are dispersed. The hydrophilic particles serve to conduct water into the hydrophobic matrix to increase the depth and degree of cure in the oral environment as compared to a similar or substantially identical formulation lacking said hydrophilic component.

7 Claims, No Drawings

SALIVA-CURED DENTAL RESTORATIVE MATERIAL

FIELD OF THE INVENTION

This invention relates to novel dental temporary filling materials and cements comprising a hydrophobic matrix in which fine, hydrophilic, water-insoluble solid particles are well dispersed to allow water to migrate into the hydrophobic material to enhance the curing behavior and final properties of the cured material.

BACKGROUND OF THE INVENTION

There are currently three major types of dental restoratives and cements that can be categorized by their method of cure. The first are self-cured materials, where the materials usually comprise a two-part system in which the curing process is initiated by mixing the two parts of the system. The second are light-cured materials wherein a generally one part system cures as a result of irradiation by high intensity light. The third are saliva-cured materials, wherein the material cures as a result of the formation of adducts between inorganic components present in the formulations with the water of the saliva, or as a result of a reaction of two or more chemical components of the formulation initiated by water of the saliva.

While the first two types are primarily used for permanent dental restorations, the third type is usually limited to temporary restorations where the material is expected to reside in the mouth for a short period of time, typically on the order of seven days or less. Ideally, a material useful for temporary applications should feature easy and fast application, short curing time, low cost, long shelf-life, good depth of cure, biocompatibility, resistance to oral fluids, satisfactory mechanical strength, ease of removal, and compatibility with permanent restoratives and cements.

Early versions of saliva-cured type temporary restoratives and cements were less than ideal and frequently generally inadequate in many respects. The curing time was generally slow (usually over 3 hours in an oral environment) making the material vulnerable to premature deterioration, especially during the hours immediately after application. The curing of the material progressed very slowly, and the depth of cure was frequently limited to a layer within a few millimeters of the contact of the material with saliva. Additionally, poor resistance to mastication forces, wear, and oral fluids frequently resulted in excessive premature deterioration of the restorations or structural failures.

SUMMARY OF THE INVENTION

In accordance with certain embodiments, there is provided a single-component dental restorative and cement formulation. The formulation comprises, consists essentially of or consists of an organic hydrophobic medium of viscous liquid or semi-solid consistency, having particles well dispersed therein to form a paste-like material, wherein such particles comprise or consist essentially of an inorganic component which, in the presence of water, undergoes a chemical reaction resulting in hardening of the formulation, and a hydrophilic fine particulate component which is insoluble in water, wherein the formulation cures upon contact with water in oral fluids, and wherein the hydrophilic component serves to conduct water into the hydrophobic medium to increase the depth and degree of cure as compared to a similar or substantially identical formulation lacking said hydrophilic component.

In accordance with certain embodiments, there is provided a single-component dental restorative and cement formulation. The formulation comprises, consists essentially of or consists of (i) an organic hydrophobic medium of viscous liquid or semi-solid consistency, having particles well dispersed therein to form a paste-like material, wherein such particles comprise or consist essentially of an inorganic component which, in the presence of water, undergoes a chemical reaction resulting in hardening of the formulation and at least 3.5% by weight of a hydrophilic fine particulate component which is insoluble in water; (ii) one or more organic acids; and (iii) one or more bivalent metal oxides, wherein the formulation cures upon contact with water in oral fluids, and wherein the hydrophilic component serves to conduct water into the hydrophobic medium to increase the depth and degree of cure as compared to a similar or substantially identical formulation lacking said hydrophilic component.

Preferred embodiments may include one or more of the following: matrix comprises petrolatum, petrolatum derivatives, natural wax and/or synthetic wax; the hydrophilic water-insoluble particles comprise fumed or precipitated silica; the inorganic component comprises calcium sulfate and/or calcium sulfate hemihydrate; the hydrophilic water-insoluble particles are present at a concentration of at least about 2.5% by weight; the one or more organic acids comprise a polycarboxylic acid; and the one or more bivalent metal oxides comprise zinc oxide.

In accordance with certain embodiments, there is provided a method of filling dental cavities and cementing dental prostheses comprising placing a portion of a formulation as described above in contact with at least one surface of a tooth, and exposing the formulation to oral fluids or water to permit curing of the formulation.

DETAILED DESCRIPTION OF THE PREFERRED EMBODIMENT

Preferred restorative materials disclosed herein allow for the manufacture of temporary restoratives and cements featuring one or more of the following characteristics: improved resistance of the final products to oral environment, faster speed and increased depth of cure as compared to prior art materials, biocompatibility, ease of application, long shelf-life, ease of removal, and compatibility with known permanent dental restoratives and cements.

The novel dental temporary filling materials and cements according to preferred embodiments comprise, consist of, and/or consist essentially of a hydrophobic matrix in which fine, hydrophilic, water-insoluble solid particles are thoroughly dispersed. Such a blend, in the presence of water or upon reaction with water, converts its physical form from the consistency of a moldable paste to a firm solid. The fine, hydrophilic, water-insoluble material that is dispersed throughout the hydrophobic material conducts the water in saliva deeper into the bulk of the hydrophobic material, greatly improving both the depth of cure and the time of cure as compared to similar or otherwise identical formulations which lack such hydrophilic particles.

The term "consisting essentially of" as used herein is used to encompass those materials having the recited elements and possibly others that do not materially affect the basic and novel characteristics of the claimed invention. For example, materials that give rise to a "secondary cure" (e.g. an anhydrous acid, polyacid or acid anhydride together with inorganic materials reactive with such acid materials) are excluded by "consisting essentially of" (unless, of course, they are expressly recited in the claim), whereas materials that do not materially affect the curing properties of the material (e.g. dyes and pigments such as titanium dioxide or iron oxide, and fluoride salts for fluoridization) are not excluded by use of this transitional phrase in a claim.

Saliva-curable dental restoratives and cements according to preferred embodiments exhibit substantial enhancement of one or more relevant characteristics, including shortening of curing time, faster progress of depth of cure and related shortening of time necessary for the restoration to withstand mastication forces, and improved resistance to oral environment before cure. In certain embodiments, the curing time of a formulation is at least 10%, at least 20%, at least 30%, or at least 40% shorter and/or a similar depth of cure is achieved at least 10%, at least 20%, at least 30%, at least 40% or at least 50% faster than similar or otherwise identical formulations which lack the above-discussed hydrophilic particles.

In formulations of saliva-cured restoratives and cements, the medium in which water-reactive components are suspended include, but are not limited to, materials of viscous liquid or semi-solid consistency such as fatty acids and their esters, polyalkalenes, mineral oils, paraffins, synthetic or natural waxes, and silicone oils. In certain preferred embodiments, petrolatum is used. These highly hydrophobic materials may be present in amounts of 20%-50% by weight, including 25%-40% by weight, and provide resilience to the aqueous environment, but they make penetration of water very slow, resulting in retardation of the curing process and in limiting progress of depth of cure.

The water-reactive component comprises inorganic solid particles which contribute, in part, to the hardening of the formulation include, but are not limited to, calcium sulfate, (including hydrated forms such as calcium sulfate hemihydrate), calcium silicate, calcium oxide, magnesium oxide, magnesium chloride, phosphate salts, colloidal silicic acid and certain organosilicone components such as alkoxysilicones. Such component may be present in amounts of 45%-80% by weight, including 50%-75% and 60-75% by weight.

Preferred embodiments disclosed herein address the problem of providing an essentially hydrophobic composition which allows for controlled penetration of water permitting the hardening process to occur at a significantly faster rate and to greater depths by dispersing highly hydrophilic, water-insoluble fine particles throughout the composition. These particles are preferably thoroughly and generally evenly dispersed in the mass of the material to be cured and may be present at amounts of about 2.5%-20% by weight, including 3%-10%, 3%-15%, 3%-20%, 3.5%-10%, 3.5%-15%, 3.5%-20%, 4%-20%, 4%-15%, 4%-10%, 5%-15% and 5-10% by weight. Suitable hydrophilic particles include, but are not limited to, precipitated and/or fumed silicas, silica gels, aluminum oxides and similar particulate materials exhibiting high surface area to weight ratios. In certain embodiments, hydrophilic silicas are preferred. It is theorized that the hydrophilic nature of such particles allows them to conduct water into the otherwise highly hydrophobic medium where the water can react with the water-reactive component to cure the material more rapidly and more fully. Their presence therefore shortens the time necessary to achieve adequate hardening of the material in the mouth and increases the depth of cure achieved after 60-90 minutes of exposure to water (usually in the form of saliva) in the oral environment. The final hardness of the material and depth of such hardness is also enhanced by the incorporation of hydrophilic material. It should be noted that curing or hardening may take any form, such as hydrating of materials, including ether-forming hydrates.

In certain embodiments, the formulation may additionally comprise a combination of materials that can provide a secondary curing mechanism. Such combination of materials includes inorganic particles, such as bivalent metal salts or oxides, that are reactive with organic acids. Suitable bivalent metal compounds include zinc oxide, calcium oxide, calcium hydroxide, magnesium oxide, barium oxide, strontium oxide, calcium carbonate, calcium silicate, magnesium silicate and/or zinc carbonate. The organic acid preferably comprises an anhydrous acid, polyacid or acid anhydride, and may be selected from polyacrylic, itaconic, tartaric, citric, maleic, oxalic or lactic acids or their copolymers. In one embodiment, the organic acid comprises a polyacrylic acid, and has an average molecular weight ranging from 2,000-250,000. Such acids are present in anhydrous form, preferably at concentrations of 1-20% of by weight in the formulation. Their reaction with alkaline particles is triggered by the presence of water.

The formulation may also include additives that affect the appearance of the material. Such additives include dyes or pigments which are used to enhance the aesthetics and to facilitate distinction of the cement from tooth structure. Preferred dyes or pigments include iron oxides or titanium dioxide. The formulations may also include fluoride releasing salts. Salts such as sodium fluoride, stannous fluoride, potassium fluorosilicate, sodium fluorosilicate, zinc hexafluorosilicate or sodium monofluoro phosphate are among those preferred.

The formulations contain ingredients that are biocompatible and non-toxic for use in the oral cavity of a human. The formulations are preferably not harmful or irritating to oral tissues, including tooth pulp, and do not give off harmful amounts of heat or produce irritating or toxic materials as part of the curing process in the mouth.

The formulations may be in the form of a filling, and may be bonded to at least a portion of a tooth. They are used in a manner that would be understood by one skilled in the art, such methods of use including placing a portion of a formulation in contact with at least one surface of a tooth and exposing the formulation to oral fluids or water to permit curing of the formulation. The formulation is preferably cured within 30 minutes, 60 minutes or 90 minutes of application.

The new embodiments disclosed herein include important and significant modifications in the composition of prior art dental temporary restoratives and cements. Such prior art cements include those of moldable paste-type consistencies that cure within 2.5-4 hours to a depth of a few millimeters. Surface consistency of such prior art materials after cure is solid but not hard, and is easily breakable when pressed with metal or plastic instruments. Hardness of the cured materials decreases rapidly with the distance from the surface where there is direct contact with moisture, largely because the water cannot adequately penetrate into the bulk of the material to achieve a good cure. Therefore, during its service time, much of the material in prior art formulations is inadequately cured.

Attempts by the present inventors to shorten the curing time necessary to achieve a desirable depth of cure, good surface hardness and stronger mechanical characteristics of the cured formulations were initially hampered by the apparent contradiction of requirements to reach such goals. The formulations of saliva-cured restoratives or cements must have hydrophobic characteristics in order to exhibit an adequate resistance to the oral environment, especially during the pre-cure period. Yet the presence of water that is necessary for curing is hindered by the highly hydrophobic nature of the material that generally excludes much water. Inclusion of hydrophilic materials in the formulation to help provide water for curing was discouraged as it was thought that it would cause the material to possibly erode prior to the time needed for cure and possibly also weaken it during its service period in the mouth. Therefore, the hydrophobic nature of the paste conflicts with the requirement of good water penetration through the bulk of the restorative or cement, which is needed to induce curing or hardening of the material.

However, when the finely dispersed, hydrophilic, water-insoluble material was included in formulations as described herein, the speed and depth of cure was increased without excessive wash-out prior to cure and was accompanied by another unexpected and highly desirable change in performance of these materials. It was generally recognized that the formulations containing calcium sulfate as the principal component responsible for their cure significantly expand during the process of hardening. Such an effect is highly undesirable as it causes stress on the tooth and may have a damaging effect on the pulp in some circumstances. It was surprisingly found that in the presence of the hydrophilic particles in the formulations disclosed herein, the expansion of the material upon curing was reduced to the point that it became insignificant.

The following Examples illustrate the unexpected properties discussed above for certain embodiments of the invention disclosed herein. Note that the Examples also illustrate the performance of other formulations which may not fall within the scope of the invention or claims, but which provide a comparison to illustrate the effect of changing the content of formulations.

Example 1

This example provides a comparison of two formulations, one (A) featuring a dual mechanism of cure: reaction of zinc oxide with polyacrylic acid; and the other (B) featuring a single mechanism of cure: hydration of calcium sulfate hemihydrate.

| Chemical composition | A | B |
|---|---|---|
| | 55% $CaSO_4 \cdot 1/2\ H_2O$ | 73% $CaSO_4 \cdot 1/2\ H_2O$ |
| | 28% Petrolatum | 26% Petrolatum |
| | 10% ZnO | |
| | 2% Polyacrylic acid | |
| | 2% Hydrophilic silica | |

| | 30 Minutes | | 60 Minutes | | 90 Minutes | |
|---|---|---|---|---|---|---|
| Batch ID | Expansion (mm) | Depth of cure (mm) | Expansion (mm) | Depth of cure (mm) | Expansion (mm) | Depth of cure (mm) |
| A | 0.00 | 0.00 | 1.00 | 4.82 | 1.38 | 6.50 |
| B | 3.30 | 4.90 | 3.30 | 9.81 | 3.30 | FC (13.98) |

FC = fully cured

Formulation B cures faster but exhibits significantly more expansion. No signs of disintegration of the materials were observed during the curing process, as evidenced by lack of haze in water environment over the time of the experiment.

Example 2

This example provides a comparison of two additional formulations differing in mechanism of cure:

| Chemical composition | A | B |
|---|---|---|
| | 73% $CaSO_4 \cdot 1/2\ H_2O$ | 63% $CaSO_4 \cdot 1/2\ H_2O$ |
| | 26% Petrolatum | 25% Petrolatum |
| | | 9% ZnO |
| | | 2% Polyacrylic acid |

| | 30 Minutes | | 60 Minutes | | 90 Minutes | |
|---|---|---|---|---|---|---|
| Batch ID | Expansion (mm) | Depth of cure (mm) | Expansion (mm) | Depth of cure (mm) | Expansion (mm) | Depth of cure (mm) |
| A | 3.30 | 4.90 | 3.30 | 9.81 | 3.30 | FC (13.98) |
| B | 1.00 | 4.86 | 1.00 | 10.80 | 1.00 | FC (11.40) |

FC = fully cured

Comparison of formulations A and B indicates expansion of the cured materials may be controlled by addition of the secondary curing mechanism without affecting depth of cure. No signs of disintegration of the material were observed during the curing process.

Example 3

This example illustrates a beneficial effect of the presence of hydrophilic fumed silica at concentrations of 5% and 10% on curing characteristics of formulations featuring hydration of calcium sulfate hemihydrate.

|  | A | B | C |
|---|---|---|---|
| Chemical composition | 73% $CaSO_4 \cdot \frac{1}{2} H_2O$<br>26% Petrolatum | 63% $CaSO_4 \cdot \frac{1}{2} H_2O$<br>30% Petrolatum<br>5% silica | 50% $CaSO_4 \cdot \frac{1}{2} H_2O$<br>39% Petrolatum<br>10% silica |

| | 30 Minutes | | 60 Minutes | |
|---|---|---|---|---|
| Batch ID | Expansion (mm) | Depth of cure (mm) | Expansion (mm) | Depth of cure (mm) |
| A: 0% silica | 3.3 | 4.9 | 3.3 | 6.5 |
| B: 5% silica | <1.0 | 4.8 | <1.0 | 6.7 |
| C: 10% silica | <1.0 | 6.3 | <1.0 | 8.4 |

The presence of silica had a pronounced beneficial effect on reducing the volumetric expansion of the composition during cure at both 5% and 10% concentration. The beneficial effect on depth of cure was more relevant at a concentration of 10% silica. Increasing the concentration of silica from 5% to 10% results in a significant increase in depth and speed of cure. No signs of disintegration of the material were observed during the curing process. Fast progress of cure in the formulation containing 10% silica eliminated the need for extending curing time beyond 60 minutes and also allows for a material to be made having a single cure mechanism without having significant expansion.

It should be understood that the above description discloses specific embodiments of the invention and are for purposes of illustration only. There may be other modifications and changes obvious to those of ordinary skill in the art that fall within the scope of the invention which should be limited only by the following claims and their legal equivalents.

What is claimed is:

1. A single-component dental restorative and cement formulation, consisting essentially of: an organic hydrophobic medium of viscous liquid or semi-solid consistency, having particles well dispersed therein to form a paste material, wherein such particles consist essentially of an inorganic component which, in the presence of water, undergoes a chemical reaction resulting in hardening of the formulation; and a hydrophilic fine particulate component which is insoluble in water; and wherein the formulation cures upon contact with water in oral fluids, and wherein the hydrophilic component serves to conduct water into the hydrophobic medium to increase the depth and degree of cure as compared to a similar or substantially identical formulation lacking said hydrophilic component.

2. The dental formulation of claim 1, wherein the organic hydrophobic medium comprises petrolatum, petrolatum derivatives, natural wax and/or synthetic wax.

3. The dental formulation of claim 1, wherein the hydrophilic water-insoluble particles comprise fumed or precipitated silica.

4. The dental formulation of claim 1, wherein the hydrophilic water-insoluble particles comprise aluminum oxide, activated alumina, molecular sieves, diatomaceous earth, bentonite or mixtures thereof.

5. The dental formulation of claim 1, wherein the inorganic component comprises calcium sulfate and/or calcium sulfate hemihydrate.

6. The dental formulation of claim 1, wherein the hydrophilic water-insoluble particles are present at a concentration of 2.5-20% by weight.

7. The dental formulation of claim 1, wherein the hydrophilic water-insoluble particles are in a form of microfibers and are present in the blend at 2.5 - 10% by weight.

\* \* \* \* \*